United States Patent [19]

Bisagni et al.

[11] Patent Number: 4,835,160
[45] Date of Patent: May 30, 1989

[54] DERIVATIVES OF PYRIDOINDOLE, HAVING ANTI-TUMOR PROPERTIES

[75] Inventors: Emile Bisagni, Orsay; Nguyen Chi Hung, Les Ulis; Odile Pepin, Toulouse, all of France

[73] Assignees: Sanofi; Centre National De La Recherche Scientifique, both of Paris, France

[21] Appl. No.: 42,896

[22] Filed: Mar. 17, 1987

[30] Foreign Application Priority Data

Mar. 17, 1986 [FR] France .................. 86 04202

[51] Int. Cl.$^4$ .................. C07D 471/04; A61K 31/44
[52] U.S. Cl. .................. 514/292; 546/86; 546/87
[58] Field of Search .................. 546/86, 87; 514/292

[56] References Cited

FOREIGN PATENT DOCUMENTS 2327783 5/1977 France .................. 546/70
2422662 11/1979 France .................. 546/64

OTHER PUBLICATIONS

Nguyen et al., Tetrahedron, vol. 43 (No. 3), pp. 527–535 (Mar. 1 1987).
Chem. Abstracts, vol. 108(7), abst. No. 55,931h, Feb. 15, 1988.
Chem. Abstracts, vol. 108(9), abst. No. 75,380–f, Feb. 29, 1988.

Primary Examiner—Alan L. Rotman
Attorney, Agent, or Firm—Wegner & Bretschneider

[57] ABSTRACT

The present invention concerns derivatives of 5H-pyrido[4,3-b]-indole with the following general formula:

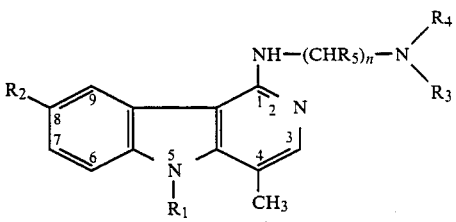

in which n represents a whole number from 2 to 4, $R_1$ represents hydrogen or a lower alkyl group; $R_2$ represents hydrogen, a hydroxy group or a lower alkyloxy group; $R_3$ and $R_4$ represents hydrogen, a lower alkyl group or hydroxyalkyl group, $R_5$ can be identical or different and represents hydrogen, a hydroxy group or a lower alkyl group, as well as the tautomeric forms and the addition salts with pharmaceutically acceptable mineral or organic acids.

The invention also concerns their preparation process, and their use as medicaments.

13 Claims, No Drawings

DERIVATIVES OF PYRIDOINDOLE, HAVING ANTI-TUMOR PROPERTIES

The invention concerns new derivatives of 5H-pyrido[4,3-b]indole, their preparation process, their use as medicaments and the compositions containing them.

These compounds, which show useful antitumourous properties, answer to the following formula (I):

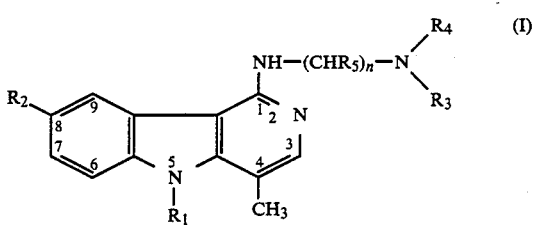

in which n represents a whole number from 2 to 4, $R_1$ represents hydrogen, or a $C_1$–$C_4$ alkyl group, $R_2$ represents hydrogen, a hydroxy group or a $C_1$–$C_4$ alkoxy group, $R_3$ and $R_4$, independently of each other, are hydrogen, a $C_1$–$C_4$ alkyl or hydroxyalkyl group, $R_5$ can be identical or different and represents hydrogen, a hydroxy group or a $C_1$–$C_4$ alkyl group.

The invention also concerns tautomeric forms with the formula (I) when they exist as well as their addition salts with pharmaceutically acceptable mineral or organic acids.

Some derivatives of 1-amino-5H-pyrido[4,3-b]indole have been described previously in the literature [C. DUROCO, A. CIVIER, J. ANDRELOUISFERT et E. BISAGNI—J. Heterocycl. Chem., 12, (5), 963–967, (1975), Ch. S. lee, T. OHTA, K. SHUDO et T. OKAMATO—Heterocycles, 16, (7), 1081–1084, (1981)].

However, these derivatives contain neither a methyl group in position -4 nor an alkylaminoalkylamino chain in position -1, which are characteristics of compounds with the formula (I).

In addition, no therapeutic activity is reported for all these derivatives.

The invention also concerns a preparation process for compounds with the formula (I) characterized in that:

a 4-methyl-2H,5H-pyrido[4,3-b]1-indolone with the formula (IV):

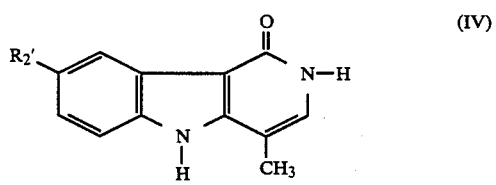

in which $R'_2$ represents hydrogen or a $C_1$–$C_4$ alkoxy group, is converted by the action of a chlorinating agent into a 1-chloro-4-methyl-5H-pyrido[4,3-b]indole with the formula (V):

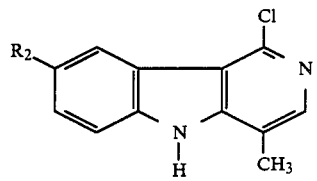

in which $R_2$ represents hydrogen or a $C_1$–$C_4$ alkoxy group, then, possibly after alkylation in position 5 by an alkyl halogenide, in order to form the compound with the formula (VI):

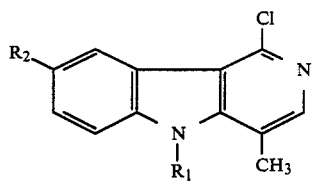

in which $R_2$ has the same significances as in formula (V) and $R_1$ represents an alkyl group in $C_1$–$C_4$, and possibly after action of a mineral acid, such as HBr or HI, the compound with the formula (V) in which $R_2$ represents an alkoxy group or the compound with the formula (VI) can be converted into 1-chloro-8-hydroxy-4-methyl-5H-pyrido[4,3-b]indole (VI: $R_1$=hydrogen or $C_1$–$C_4$ alkyl; $R_2$=a hydroxy group), the compound with the formula (V), or the formula (VI), is condensed with an amine with the formula:

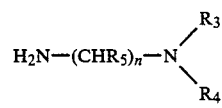

in which n, $R_3$, $R_4$ and $R_5$ are as defined for formula (I).

The compound with the formula (IV) can be prepared for example in the following way:

4-hydroxy-5-methyl-1H-2-pyridone below of which the synthesis

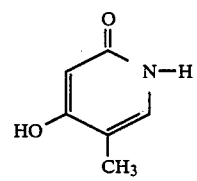

has been described by E. BISAGNI and N. CHI HUNG (Synthesis, 1984, 765), put to react at a high temperature with a phenylhydrazine with the formula:

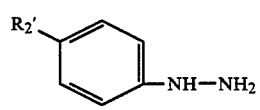

in which $R_2$ represents hydrogen or an alkoxy group, leads to 4-methyl-2H-5H-pyrido[4,3-b]1-indolon with the formula (IV).

The following non-limiting examples are given as an illustration of the invention.

EXAMPLE 1:

Preparation of
1-chloro-4-methyl-5H-pyrido[4,3-b]indole (compound with the formula (V) in which $R_2=H$)

(A) 4-methyl-2H,5H-pyrido[4,3-b]1-indolone (compound with the formula (IV) in which $R_2=H$)

A mixture formed by 4-hydroxy-5-methyl-1H-1-pyridone (4.1 g), phenylhydrazine freshly distilled (9.5 ml) and diphenylether (70 ml) is heated to reflux for 2 hours, eliminating the water formed by a DEAN-STARK apparatus, then distilling off the excess phenylhydrazine, and the resulting mixture is cooled to ambient temperature. After addition of 100 ml of toluene, the precipitate formed is separated, washed with toluene and taken up in 100 ml of boiling dioxane in which it is very slightly soluble.

5.5 g of clear beige microcrystals are obtained.

Yield: 88%; m.p.>260° C.

Calculated for $C_{12}H_{10}N_2O$; 0.75 $H_2O$: C, 68.08; H, 5.43; N, 13.24. Found: C, 68.49; H, 5.28; N, 13.31.

NMR H1 [$(CD_3)_2SO$], δ: 2.32 (s, 3H,$CH_3$), 7.18 (s widened, 1H,H-3), 7.19–7.52 (m, 3H,H-6+H-7+H-8), 8.08 (q, 1H,H-9), 10.94 (s wide, 1H,NH-5 11.75 (s, 1H,NH-2).

(B) 1-chloro-4-methyl-5H-pyrido[4,3-b]indole (compound with the formula (V) in which $R_2=H$)

A mixture of 4-methyl-2H,5H-pyrido[4,3-b]1-indolone (1.6 g) in phenylphosphonic acid dichloride (120 ml) is heated to 160°–165° C., under agitation, for 4 hours and the excess of the chlorination agent is evaporated under reduced pressure (2 mm). The residue is taken up in 400 ml of hot 0.5N hydrochloric acid, filtered and the filtrate is alkalinized by ammonia. The precipitate obtained, separated and dried, is recrystallized in xylene in order to give colourless leaflets (1.3 g).

Yield: 81%; m.p.>260° C.

Calculated for $C_{12}H_9ClN_2$: C, 66.52; H, 4.19; N, 12.93; Cl, 16.36. Found: C, 66.26; H, 4.18; N, 12.91; Cl, 16.28.

NMR H1 [$(CD_3)_2SO$]; δ: 2.55 (s, 3H,CH3-4), 7.3–7.73 (m, 3H,H-68.09 (s wide, 1H,H-3), 8.40 (d, 1H,H-9), 12.11 (s wide, 1H,NH-5).

EXAMPLE 2

Preparation of
1-chloro-8-methoxy-4-methyl-5H-pyrido[4,3-b]-indole (compound with the formula (V) in which $R_2=-OCH_3$)

(A)
4-methyl-8-methoxy-2H,5H-pyrido[4,3-b]1-indolone (compound with the formula (IV) in which $R_2=-OCH_3$)

The reaction is carried out starting from a suspension of 2.11 g (16.8 mmoles) of 4-hydroxy-5-methyl-1H-2-pyridone in 60 ml of diphenylether degassed with argon at boiling point, and from a solution of 4-methoxy phenylhydrazine (7 g, 50.4 mmoles), dried under vacuum after having been freed from its hydrochloride in 80 ml of diphenylether, also degassed with argon, but at ambient temperature, which solution is added to the previous boiling suspension, maintained under argon and under agitation. The mixture is heated to reflux for 6 hours, eliminating the water formed by a DEAN-STARK apparatus, cooled and 150 ml of toluene is added to it. The precipitate formed is filtered off, washed with toluene and with pentane, dried and put in suspension in 100 ml of an N sodium hydroxide solution. The insoluble product is filtered off, then recrystallized in the minimum of ethanol to give 660 mg of colourless microcrystals, corresponding to the partially hydrated expected compound.

Yield: 17.1%; m.p.>260°.

Calulated for $C_{13}H_{12}N_2O_2$; 0.33$H_2O$: C, 66.68; H, 5.41; N, 11.97. Found: C, 66.63; H, 5.26; N, 11.99.

NMR H1 [$(CD_3)_2SO$]; δ: 2.26 (s, 3H,CH3-4), 3.84 (s, 3H,$OCH_3$), 6.94 (q, 1H,H7,$J_{7-6}=8.6$ Hz, $J_{7-9}=2.8$ Hz), 7.07 (s widened, 1H,H-3), 7.43 (d, 1H,H-6), 7.65 (d, 1H,H-9), 10.82 (s wide, 1H,NH-5), 11.55 (s wide, 1H, NH-2).

(B)
1-chloro-4-methyl-8-methoxy-5H-pyrido[4,3-b]indole (compound with the formula (V) in which $R_2=OCH_3$)

720 mg of the compound previously obtained is heated in phosphorous oxychloride (60 ml) to reflux for 3 hours and the excess oxychloride is evaporated under reduced pressure. The residue is taken up in 100 ml of boiling water, the mixture is heated to boiling point for 3 minutes and filtered. The filtrate is alkalinized cold by ammonia and the precipitate formed is separated, dried then recrystallized from acetonitrile to give 580 mg of yellow microcrystals.

Yield: 76.5%; m.p.=243°–245° C.

Calulated for $C_{13}H_{11}ClN_2O$: C, 63.29; H, 4.49; N, 11.35; Cl, 14.37. Found: C, 63.48; H, 4.56; N, 11.15; Cl, 14.64.

NMR H1 [$(CD_3)_2SO$]; δ: 2.52 (d, 3H,CH3-4,$J_{CH_3-H-3}=1$ Hz), 3.91 (s, 3H,$OCH_3$) 7.23 (q, 1H,H-7,$J_{7-6}=9$ Hz, $J_{7-9}=2.5$ Hz), 7.60 (d, 1H,H-6), 7.87 (d, 1H,H-9), 8.04 (d, 1H,H-3).

EXAMPLE 3

Preparation of
1-chloro-4,5-dimethyl-8-methoxy-5H-pyrido[4,3-b]-indole (compound with the formula (VI) in which $R_1=-CH_3$ and $R_2=-OCH_3$)

600 mg of 1-chloro-4-methyl-8-methoxy-5H-pyrido[4,3-b]indole disolved in 20 ml of N,N-dimethylformamide is treated by methyl iodide (0.3 ml: 2 equivalents) in the presence of potassium carbonate (1.7 g; 5 equivalents) at ambient temperature for 5 hours. After evaporation of the solvent under reduced pressure, the product obtained is taken up by 20 ml of water which is then acidified by an N aqueous solution of hydrochloric acid, then neutralized by an ammonia solution. The precipitate obtained is filtered off, washed with water, dried and recrystallized from cyclohexane.

Yield: 82%; m.p.=173°–176° C.

Calculated for $C_{14}H_{13}ClN_2O$: C, 64.49; H, 5.03; N, 10.74; Cl, 13.60. Found: C, 64.45; H, 5.29; N, 10.58; Cl, 13.31.

NMR H1 [$(CD_3)_2SO$]; δ: 2.28 (d, 3H,CH3-4,$J_{CH_3-H-3}=1$ Hz), 3.91 (s, 3H,$OCH_3$), 4.14 (s, 3H,$NCH_3$), 7.29 (q, 1H,H-7,$J_{7-6}=8.9$ Hz,$J_{7-9}=2.5$ H 7.70 (d, 1-H,H-6) 7.91 (d, 1H,H-9), 8 (d, 1H,H3).

EXAMPLE 4

Preparation of
1-chloro-8-hydroxy-4-methyl-5H-pyrido[4,3-b]indole
(compound with the formula (VI) in which $R_1=H$ and $R_2=OH$)

1-chloro-4-methyl-8-methoxy-5H-pyrido[4,3-b]indole (200 mg) is heated to reflux of a concentrated aqueous solution of hydrobromic acid (7 ml) for 1 hour 30 minutes. After cooling, the medium is poured into water then neutralized with ammonia. The precipitate formed is filtered off, then purified by chromatography on a silica column ($CH_2Cl_2/C_2H_5OH$; 98/2) isolating the fraction of which the Rf is 0.55 in chromatography on thin layer silica. ($CH_2Cl_2/C_2H_5OH$; 9/1).

Yield: 74.8%; Sublimation above 265°.

Calculated for $C_{12}H_9ClN_2O$: C, 61.95; H, 3.90; N, 12.04: Cl, 15.24. Found: C, 62.01; H, 3.83; N, 11.97; Cl, 14.97.

NMR H1 [$(CD_3)_2SO$]; δ: 2.52 (d, 3H,$CH_3$-4), 7.08 (q. 1H,H-7,$J_{7-6}J_{7-9}$=2.4 Hz), 7.49 (d, 1H,H-6), 7.78 (d, 1H,H-9), 8.02 (d, 1H,H-3, $J_{H-3-CH3-4}$=1.2 Hz), 9.26 (s, wide, 1H,OH), 11.8 (s wide, 1H,NH-5).

EXAMPLE 5

Preparation of
1-chloro-4,5-dimethyl-8-hydroxy-5H-pyrido[4,3-b]indole (compound with the formula (VI) in which $R_1$=—$CH_3$ and $R_2$=—OH)

1-chloro-4,5-dimethyl-8-methoxy-5H-pyrido[4,3-b]indole is treated by a concentrated aqueous solution of hydrobromic acid according to the operating method of example 4. The precipitate obtained after neutralization by an ammonia solution is directly recrystallized from dioxane.

Yield: 65%; m.p.>260° C.

Calculated for $C_{13}H_{11}ClN_2O$: C, 63.29; H, 4.49; N, 11.35; Cl, 14.37. Found: C, 63.48; H, 4.52; N, 11.35; Cl, 13.92.

NMR H1 [$(CD_3)_2SO$]; δ: 2.76 (d, 3H,$CH_3$-4,$J_{CH3-H-3}$=1 Hz), 4.10 (s, 3H,N-$CH_3$), 7.12 (q, 1H,H-7,$J_{7-6}$=9 Hz, $J_{7-9}$=2.4 Hz), 7.58 (d, 1H,H-6) 7.84 (d, 1H,H-9), 7.96 (d, 1H,H-3), 9.34 (s, 1H,OH).

EXAMPLE 6:

Preparation of 1-(3-diethylamino propylamino) 4-methyl-5H-pyrido-[4,3-b]indole and of its dimaleate (SR 95400A) derivative no. 1 (I: $R_1=R_2=H$, $R_3=R_4=C_2H_5$, $R_5=H$, n=3)

1-chloro-4-methyl-5H-pyrido[4,3-b]indole (0.5 g) is dissolved in 3-diethylamino propylamine (10 ml). The reactional mixture is brought to reflux for 48 hours. Then the excess amine is distilled off under reduced pressure. The residue is taken up in 10 ml of water, then alkalinized by a concentrated aqueous solution of sodium hydroxide and finally extracted by methylene chloride.

The organic phase is dried, then concentrated under reduced pressure. The crude product thus obtained is purified by chromatography on an alumina column, first of all eluting by methylene chloride then with a mixture of methylene chloride-methanol (98/2).

The pure base thus obtained is dissolved in an acetone solution of maleic acid (at least 2 molar equivalents) which is kept boiling for 2 minutes.

After cooling the dimaleate precipitates. It is filtered off and dried.

Yield: 57%; m.p.=174°-178° C. with decomposition.

Calculated for $C_{27}H_{34}N_4O_8$: C, 59.77; H, 6.32; N, 10.33. Found: C, 59.40; H, 6.10; N, 10.62.

NMR H1 ($D_2O$); δ: 1.36 (t, 2×3H,$CH_3$—$CH_2$), 2.03-2.06 (m, 2H,$CH_2$-β), 2.35 (d, 3H,$CH_3$-4), 3.22-3.64 (m, 4×2H,$CH_2CH_3$+$CH_2$-γ+$CH_2$-α), (s, 4H,CH=CH maleate), 7.38 (d, 1H,H-3,$J_{H-3}$-$CH_3$-4=1 Hz), 7.44-7.59 (m, 3H,H-6+H-7+H8), 7.95 (d, 1H,H-9).

EXAMPLE 7:

Preparation of 1-(3-dimethylamino propylamino)-4-methyl-5H-pyrido-[4,3-b]indole and its dimaleate (SR 95403A), derivative no. 2 (I: $R_1=R_2=H$, $R_3=R_4=CH_3$, $R_5=H$, n=3)

This compound is prepared according to the operating method of example 6 at reflux of the 3-dimethylamino propylamine for 96 hours.

After chromatography, the base is recrystallized from toluene.

Yield: 50%; m.p.=163°-164° C.

Calculated for $C_{17}H_{22}N_4$: C, 72.30; H, 7.85; N, 19.84. Found: C, 72.18; H, 7.76; N, 19.77.

It is converted in a similar way into dimaleate.
m.p.=212°-213° C.

Calculated for $C_{25}H_{30}N_4O_8$: C, 58.36; H, 5.88; N, 10.89. Found: C, 58.32; H, 5.74; N, 10.44.

NMR H1 ($D_2O$); δ: 2.1-2.38 (m, 2H,$CH_2$-β), 2.47 (s, 3H,$CH_3$-4), 2.98 (s, 2×3H,N($CH_3$)$_2$), 3.3-3.5 (m, 2H,$CH_2$-γ), 3.75 (t, 2H,$CH_2$-α), 6.29 (s, 4H,CH=CH—maleate), 7.5-7.8 (m, 4H,H-3+H-6+H-7+H-8), 8.17 (d, 1H,H-9).

EXAMPLE 8

Preparation of 1-(2-hydroxyethylamino ethyl amino)-4-methyl-5H-pyrido[4,3b]indole and its dimaleate (SR 95404A), derivative no. 3 (I: $R_1=R_2=H$, $R_3=H$, $R_4=CH_2$—$CH_2$ OH, $R_5=H$, n=2)

This compound is prepared according to the operating method of example 6 in 2-hydroxyethylamino ethylamine taken to 170° C. for 16 hours.

The crude base obtained crystallizes directly, it is recrystallized from toluene.

Yield: 47%; m.p.=164°-166° C.

Calculated for $C_{16}H_{20}N_4O$: C, 67,58; H, 7.09, N, 19.71. Found: C, 67.75; H, 7.09; N, 19.46.

NMR H1 [$(CD_3)_2SO$]; δ: 2.38 (s, 3H,$CH_3$-4), 2.69 (t, 2H,NH—$CH_2CH_2$.88 (t, 2H,$CH_2$-β), 3.51 (t, 2H,NH—$CH_2$—$CH_2$—OH), 3.61 (t, 2H,$CH_2$-α 4.45 (s wide, 1H,OH), 6.13 (t, 1H-NH-1), 7.16-7.6 (m, 3H,H-6+H-7+H-8), 7.76 (s, 1H,H-3), 8.2 (d, 1H-H-9), 11.03 (s wide, 1H,NH-5).

It is converted in a similar way into dimaleate.
m.p.=205° C.

Calculated for $C_{24}H_{28}N_4O_9$: C, 55.80; H, 5.46; N, 10.85, Found: C, 55.82; H, 5.42; N, 10.67.

EXAMPLE 9

Preparation of 1-(3-diethylamino propylamino)-8-methoxy-4-methyl-5H-pyrido[4,3-b]indole and its dimaleate (SR 95700A), derivative no. 4 (I: $R_1=H$, $R_2=OCH_3$, $R_3=R_4=C_2H_5$, $R_5=H$, n=3) .

This compound is prepared by the action of 1-chloro-4-methyl-8-methoxy-5H-pyrido[4,3-b]indole on 3-diethylamino propylamine taken to reflux for 96 hours, following the operating method of example 6.

After purification by chromatography, the base is converted into dimaleate.

Yield: 62%; m.p.=176°-178° C.

Calculated for $C_{28}H_{36}N_4O_9$, $H_2O$: C, 56.95; H, 6.44; N, 9.45. Found: C, 56.72; H, 6.30; N, 9.61.

NMR H1 ($D_2O$): δ: 1.41 (t, 2×3H,$CH_3$—$CH_2$), 2.22 (m, 2H,$CH_2$-β), 2.36 3H, $CH_3$-4), 3.38 (m, 6H,3×2H,$CH_2CH_3$+$CH_2$-γ), 3.64 (t, 2H,$CH_2$ (s, 3H, $OCH_3$), 6.16 (s, 4H,CH=CH maleate), 7.17 (q. 1H,H-7,$J_{7-6}$=9 Hz,$J_{7-9}$=2.3 Hz), 7.36 (d, 1H,H-6), 7.4 (s wide, 1H,H-9), 7.48 (s, 1H,H-3).

EXAMPLE 10

Preparation of 1-(3-ethylamino propylamino)-8-methoxy-4-methyl-5H-pyrido[4,3-b]indole and its dimaleate (SR 95701A), derivative no. 5 (I: $R_1$=H, $R_2$=$OCH_3$, $R_3$=H, $R_4$=$C_2H_5$, $R_5$=H, n=3)

This compound is prepared according to the operating method of example 9 at reflux of 3-ethylamino propylamine for 96 hours.

After purification by chromatography, the base is converted into dimaleate.

Yield: 80.8%; m.p.=212°-214° C.

Calculated for $C_{26}H_{32}N_4O_9$; 0.5$H_2O$: C, 56.42; H, 5.97; N, 10.12. Found C, 56.47; H, 6.01; N, 10.02.

NMR H1 ($D_2O$): δ: 1.41 (t, 3H,$CH_3$—$CH_2$), 2.2 (m, 2H,$CH_2$-β), 2.38 (s, 3H,$CH_3$-4), 3.2 (m, 4H,$CH_2$—$CH_3$+$CH_2$-γ), 3.68 (t, 2H,$CH_2$-α) (s, 3H,$OCH_3$), 6.2 (s, 4H,CH=CH maleate), 7.31 (q, 1H,H-7,$J_{7-6}$=11 Hz, $J_{7-9}$=2.5 Hz), 7.37 (d, 1H,H-6), 7.44 (m, 1H,H-9), 7.54 (s, 1H,H-3).

EXAMPLE 11

Preparation of 1-(3-diethylamino propylamino)-4,5-dimethyl-8-methoxy-5H-pyrido[4,3-b]indole and its dimaleate (SR 95699A), derivative no. 6 (I: $R_1$=$CH_3$, $R_2$=$OCH_3$, $R_3$=$R_4$=$C_2H_5$, $R_5$=H, n=3).

This compound is prepared by the action of 1-chloro-4,5-dimethyl-8-methoxy-5H-pyrido[4,3-b]indole on 3-diethylamino propylamine taken to reflux for 44 hours, following the operating method of example 6.

The base is recrystallized from hexane.

Yield: 85.5%; m.p.=107°-109° C.

Calculated for $C_{21}H_{30}N_4O$: C, 71.15; H, 8.53; N, 15.81. Found: C, 70.96; H, 8.64; N, 15.57.

NMR H1 [$(CD_3)_2SO$]; δ: 0.99 (t, 2×3H,$CH_3$—$CH_2$), 1.81 (m, 2H,$CH_2$-2.50-2.54 (m, 3×2H,($CH_2$—$CH_3$)+$CH_2$-γ), 2.62 (d, 3H,$CH_3$-4,$J_{CH3-H}$-3Hz), 3.60 (m, 2H,$CH_2$-α), 3.90 (s, 3H,$OCH_3$), 4.05 (s, 3H,$NCH_3$), 6.35 (t, 1H,NH), 7.09 (q, 1H,H-7, $J_{7-6}$=9 Hz, $J_{7-9}$=2.3 Hz), 7.52 (d, 1H,H-6), 7.69 (d, 1H,H-3), 7.74 (d, 1H,H-9).

Then it is converted into dimaleate.

m.p.=275°-276° C.

Calculated for $C_{29}H_{38}N_4O_9$: C, 59.37; H, 6.53; N, 9.55. Found: C, 59.20; H, 6.59; N, 9.53.

EXAMPLE 12

Preparation of 1-(diethylamino propylamino)-8-hydroxy-4-methyl-5H-pyrido[4,3-b]indole and of its dimaleate (SR 95444A), dirivative no. 7, and of its dihydrochloride SR95444B, derivative no. 8 (I: $R_1$=H, $R_2$=OH, $R_3$=$R_4$=$C_2H_5$, $R_5$=H, n=3)

3-diethylamino propylamine (15 ml) and 1-chloro-8-hydroxy-4-methyl-5H-pyrido[4,3-b]indole (800 mg) are heated on a bath of oil at 170° C. for 18 hours and the excess amine is eliminated under reduced pressure. The residue is taken up in 50 ml of water, extracted with methylene chloride in which the product seems slightly soluble and the new residue obtained after evaporation of the solvent is chromatographed on an alumina column (35×2.2 cm) eluting with pure methylene chloride (300 ml), with a mixture of methylene chloride-ethanol 95/5 v/v (400 ml), then finally with the same mixture, in a proportion of 9/1 v/v (300 ml). The evaporation of this last fraction leaves a product which is dissolved in acetone (50 ml) and poured into a maleic acid solution (1 g) in 50 ml of boiling acetone. The precipitate formed is separated, agitated in suspension in 50 ml of methylethylketone for 48 hours, separated and dried in order to give 740 mg of yellowish micro-crystals corresponding to the expected dimaleate, hydrated with one molecule of water.

Yield: 41%; m.p.=200° C. with decomposition.

Calculated for $C_{27}H_{34}N_4O_9$; $H_2O$: C, 56.24; H, 6.29; N, 9.72. Found: C, 56.21; H, 6.27; N, 9.74.

Free base: recrystallizes from toluene giving pale yellow microcrystals. m.p.=125° C.

Calculated for $C_{19}H_{26}N_4O$; 0.5$H_2O$: C, 68.06; H, 8.06; N, 16.72. Found: C, 68.09; H, 8.14; N, 16.55.

NMR H1 [$(CD_3)_2SO$]; δ: 1.0 (t, 2×3H,$CH_3$—$CH_2$), 1.80 (m, 2H,$CH_2$- (s, 3H,$CH_3$-4), 2.4-2.69 (m, 6H,$CH_2$—$CH_3$+$CH_2$-γ), 3.55 -(q, 2H,$CH_2$ 6.22 (t, 1H,NH-1), 6.87 (q. 1H,H-7,$J_{7-6}$=8.5 Hz,$J_{7-9}$=2.2 Hz), 7.31 (d, 1H,H-6), 7.52 (d, 1H,H-9), 7.66 (s, 1H,H-3), 8.82 (s wide, 1H,OH-811.05 (s, 1H,NH-5).

The free base is dissolved in ethanol to which a solution of hydrochloric acid in ethyl ether is then added. After cooling, the hydrochloride precipitates. It is filtered off, washed with ethyl ether, then recrystallized from ethanol.

Yield: 72%; m.p.=208° C.

Calculated for $C_{19}H_{28}N_4OCl_2$; 2.4$H_2O$: C, 51.48; H, 7.45; N, 12.64. Found: C, 51.41; H, 7.05; N, 12.67.

EXAMPLE 13

Preparation of 1-(3-dimethylamino propylamino)-8-hydroxy-4-methyl-5H-pyrido[4,3-b]indole SR 95443 (derivative no. 9) and its dimaleate SR 95443 A (derivative no. 10) (I: $R_1$=H, $R_2$=OH, $R_3$=$R_4$=$CH_3$, $R_5$=H, n=3)

This compound is prepared according to the operating method of example 12 in the presence of 3-dimethylamino propylamine, taken to 180° C. in an autoclave for 24 hours. After purification by chromatography, the base is recrystallized from toluene.

Yield: 78%; m.p.=235°-245° C. with decomposition.

Calculated for $C_{17}H_{22}N_4O$: C, 68.43; H, 7.43; N, 18.78. Found: C, 68.42; H, 7.51; N, 18.54.

NMR H1 [$(CD_3)_2SO$]; δ: 1.83 (m, 2H,$CH_2$-β), 2.26 (s, 2×3H,N($CH_3$)$_2$(d, 3H,$CH_3$-4), 2.38-2.57 (m, 2H,$CH_2$-γ), 3.59 (m, 2H,$CH_2$-α), 6.44 (t, 1H,NH-1), 6.90 (d, 1H,H-7,$J_{7-6}$=8.5 Hz,$J_{7-9}$=2 Hz), 7.33 (d, 1H,H-6), 7.52

(d, 1H,H-9), 7.68 (d, 1H,H-3,JH-3-CH$_3$-4=1 Hz), 8.82 (s wide, 1H,OH-8), 11.06 (s wide, 1H,NH-5).

Its dimaleate is prepared in the usual way.

m.p.=210°–220° C. with decomposition.

Calculated for C$_{17}$H$_{22}$N$_4$O; 2C$_4$H$_4$O$_4$: 0.5H$_2$O: C, 55.65; H, 5.75; N, Found: C, 55.50; H, 5.74; N, 10.39.

EXAMPLE 14

Preparation of 1-(3-diethylamino propylamino)-4,5-dimethyl-8-hydroxy-5H-pyrido[4,3-b]indole, of its dimaleate SR 95646 A (derivative no. 11) and of its dihydrochloride SR 95646 B (derivative no. 12) (I: R$_1$=CH$_3$, R$_2$=OH, R$_3$=R$_4$=C$_2$H$_5$, R$_5$=H, n=3)

This compound is prepared according to the operating method of example 12 at reflux of 3-diethylamino propylamine for 72 hours.

The base is recrystallized from ethyl acetate.

Yield: 49%; m.p.=187°–189° C.

Calculated for C$_{20}$H$_{28}$N$_4$O: C, 70.55; H, 8.29; N, 16.46. Found: C, 70.30; H, 8.21; N, 16.17.

NMR H1 [(CD$_3$)$_2$SO]; δ: 1.0 (t, 2×3H,CH$_3$—CH$_2$), 1.81 (m, 2H,CH$_2$- (m, 3×2H, CH$_2$—CH$_3$+CH$_2$-γ), 2.60 (d, 3H,CH$_3$-4), 3.58 (q, 2H,CH$_2$4.02 (s, 3H,NCH$_3$), 6.28 (m, 1H,NH-1), 6.95 (q, 1H,H-7,J$_{7-6}$=8.7 Hz, J$_{7-9}$=2.2 Hz), 7.40 (d, 1H,H-6), 7.56 (d, 1H,H-9), 7.66 (d, 1H,H-3,JH-38.92 (s wide, 1H,OH).

It is then converted into dimaleate:

m.p.=176°–178° C.

Calculated for C$_{20}$H$_{28}$N$_4$O,C$_8$H$_8$O$_8$: C, 58.73; H, 6.34; N, 9.79. Found: C, 58.51; H, 6.61; N, 9.84.

Starting from the free base, the hydrochloride is prepared as in example 12.

Yield 85%; m.p.=200° C.

Calculated for C$_{20}$H$_{30}$N$_4$OCl$_2$; 1.25H$_2$O: C, 55.10; H, 7.51; N, 12.85. Found: C, 55.16; H, 7.58; N, 12.73.

EXAMPLE 15

Preparation of 4,5-dimethyl-1-(3-dimethylamino propylamino)-8-methoxy-5H-pyrido[4,3-b]indole dihydrochloride SR 26125 A (derivative no. 13) (I: R$_1$=CH$_3$, R$_2$=OCH$_3$, R$_3$=R$_4$=CH$_3$, R$_5$=H, n=3)

This compound is prepared according to the operating method of example 6 starting from 1-chloro-4,5-dimethyl-8-methoxy-pyrido[4,3-b]indole in the presence of 3-dimethylamino propylamine taken to 200° C. in an autoclave for 4 hours. After purification by chromatography (eluent: methanol/triethylamine; 9/1) the pure base is isolated.

Yield: 61%; m.p.=108° C.

The base is converted into hydrochloride as in example 12.

Yield: 92%; m.p.=200° C.

Calculated for C$_{19}$H$_{28}$N$_4$OCl$_2$; 2.25H$_2$O: C, 51.89; H, 7.45; N, 12.73. Found: C, 51.93; H, 7.34; N, 12.66. NMR H1 [D$_2$O+CF$_3$CO$_2$D]; δ: 2.25–2.50 (m, 2H,CH$_2$-β), 2.56 (s, 3H, 3.12 (s, 2×3H,N-CH$_3$), 3.40–3.59 (m, 2H,CH$_2$-γ), 3.71–3.90 (m, 2H,CH$_2$-α), 3.78 (s, 3H,CH$_3$-5), 4.03 (s, 3H,O—CH$_3$), 7.16 (q, 1H,H-7,J$_{7-6}$=10 H J$_{7-9}$=2.5 Hz), 7.36 (d, 1H,H-6), 7.47 (d, 1H,H-9), 7.50 (s, 1H,H-3).

EXAMPLE 16

Preparation of 4,5-dimethyl 1(3-dimethylamino propylamino)-8-hydroxy-5H-pyrido[4,3-b]indole, of its dimaleate SR 95647 A (derivative no. 14) and of its dihydrochloride SR 95647 B (derivative no. 15) (I: R$_1$=CH$_3$, R$_2$=OH, R$_3$=R$_4$=CH$_3$, R$_5$=H, n=3)

This compound is prepared according to the operating method of example 12 at reflux of 3-dimethylamino propylamine for 14 hours.

The base is recrystallized from ethyl acetate.

This compound can also be prepared starting from derivative no. 13 according to the operating method of example 20.

Yield: 50.5%; Sublimation above 260° C.

Calculated for C$_{18}$H$_{24}$N$_4$O: C, 69.20; H, 7.75; N, 17.94. Found: C, 69.17; H, 7.79; N, 17.65.

NMR H1 [(CD$_3$)$_2$SO]; δ: 1.83 (m, 2H,CH$_2$-β), 2.25 (s. 2×3H,N(CH$_3$)$_2$(m,2H,CH$_2$-γ), 2.61 (s, 3H,CH$_3$-4), 3.6 (m, 2H,CH$_2$-α), 4.02 (s, 3H,NCH 6.51 (s, 1H,NH), 6.97 (q, 1H,H-7,J$_{7-6}$=8.8 Hz,J$_{7-9}$=2.4 Hz), 7.41 (d, 1H,H-6), 7.54 (d, 1H,H9), 7.67 (s, 1H,H-3), 8.94 (s wide, 1H,OH).

It is converted into dimaleate.

m.p.=208°–210° C.

Calculated for C$_{18}$H$_{24}$N$_4$O, C$_8$H$_8$O$_8$, ½H$_2$O: C, 56.42; H, 5.96; N, 10.12. Found: C, 56.52; H, 6.15; N, 10.53.

The dihydrochloride is prepared starting from the base as in example 13.

Yield: 89%; m.p.=258° C.

Calculated for C$_{18}$H$_{26}$N$_4$OCl$_2$; 1.25H$_2$O: C, 53.01; H, 6.73; N, 13.73. Found: C, 52.85; H, 7.06; N, 13.53.

EXAMPLE 17

Preparation of 1-(3-diethylamino propylamino)-4,5-dimethyl-5H-pyrido[4,3-b]indole dihydrochloride, SR 26021 A (derivative no. 16) (I: R$_1$=CH$_3$, R$_2$=H, R$_3$=R$_4$=C$_2$H$_5$, R$_5$=H, n=3)

(A) 1-chloro-4,5-dimethyl-5H-pyrido[4,3-b]indole 11.5 g (0.08 mole) of potassium carbonate, then 4.7 g (0.033 mole) of methyl iodide are added to a solution of 1-chloro-4-methyl-5H-pyrido[4,3-b]indole (3.3 g; 0.015 mole), prepared according to the operating method of example 1, in 100 ml of dry N,N-dimethylformamide. Under a nitrogen atmosphere, the medium is agitated for 5 hours at ordinary temperature. After concentration under reduced pressure at 25° C., the product obtained is dissolved in an N aqueous solution of hydrochloric acid.

Then the aqueous solution is neutralized by ammonia. The precipitate obtained is filtered, washed with water, then with acetone. The chlorinated derivative thus obtained is purified by chromatography on silica (eluent: ethyl acetate).

Yield: 59%; m.p.=214° C.

Calculated for C$_{13}$H$_{11}$N$_2$Cl: C, 67.67; H, 4.81; N, 12.14; Cl, 15.37. Found: C, 67.59; H, 4.73; N, 11.93; Cl, 15.77.

(B) 1-(3-diethylamino propylamino)-4,5-dimethyl-5H-pyrido[4,3-b]-indole dihydrochloride This compound is prepared according to the operating method of example 6 starting from the chlorinated derivative obtained in the previous stage, in the presence of 3-diethylamino propylamine taken to 200° C. in an autoclave for 6 hours. After purification by chromatography (eluent: methanol/triethylamine; 9/1), the pure base is isolated in the form of oil. It is converted into hydrochloride as in example 12.

Yield: 39%; m.p.=222° C.

Calculated for $C_{20}H_{30}N_4Cl_2$; 2.75$H_2O$: C, 53.75; H, 8.01; N, 12.53; Cl, 15.86. Found: C, 53.56; H, 8.06; N, 12.33; Cl, 16.03.

EXAMPLE 18:

Preparation of 4,5-dimethyl 1-(3-dimethylamino propylamino)-5H-pyrido[4,3-b]indole dihydrochloride, SR 26022 A (derivative no. 17) (I: $R_1=CH_3$, $R_2=H$, $R_3=R_4=CH_3$, $R_5=H$, n=3)

This compound is prepared according to the operating method of example 17 in the presence of 3-dimethylamino propylamine.

Yield: 63%; m.p.=250° C.

Calculated for $C_{18}H_{26}N_4Cl_2$; 1.5$H_2O$: C, 54.55; H, 7.37; N, 14.13. Found: C, 54.60; H, 7.50; N, 13.98.

EXAMPLE 19

Preparation of 1-(2-diethylamino ethylamino)-4,5-dimethyl-8-methoxy-5H-pyrido[4,3-b]indole dihydrochloride, SR 26152 A (derivative no. 18) (I: $R_1=CH_3$, $R_2=OCH_3$, $R_3=R_4=C_2H_5$, $R_5=H$, n=2)

This compound is prepared according to the operating method of example 6 starting from 1-chloro-4,5-dimethyl-8-methoxy-5H-pyrido[4,3-b]indole obtained in example 3 in the presence of 2-diethylamino ethylamine taken to 200°–210° C. in an autoclave for 4 hours. The base, after purification by chromatography (eluent: methanol) is converted into hydrochloride according to the operating method of example 12.

Yield: 83%; m.p.=236° C.

Calculated for $C_{20}H_{30}N_4OCl_2$; 0.5$H_2O$: C, 56.80; H, 7.40; N, 13.26; Cl, 16.80. Found: C, 57.00; H, 7.24; N, 13.27; Cl, 16.80.

NMR H1 ($D_2O$); δ: 1.47 (t, 2×3H,$CH_2$—$CH_3$), 2.44 (d, 3H,$CH_3$-4, J$CH$3.34–3.62 (m, 3×2H,$CH_2$—$CH_3$ and $CH_2$-β), 3.50 (s, 3H,$CH_3$-5), 3.90–4.09 (t, 2H,$CH_2$-α), 3.99 (s, 3H,$OCH_3$), 6.98 (q, 1H,H7,$J_{7-6}$=8.9 Hz, $J_{7-9}$=2.2 Hz), 7.14 (d, 1H,H-6), 7.34 (d, 1H,H-9), 7.45 (d, 1H,H-3).

EXAMPLE 20

Preparation of 1-(2-diethylamino ethylamino)-4,5-dimethyl-8-hydroxy-5H-pyrido[4,3-b]indole dihydrochloride, SR 26153 A (derivative no. 19) (I: $R_1=CH_3$, $R_2=OH$, $R_3=R_4=C_2H_5$, n=2)

3 g of 1-(2-diethylamino ethylamino) 4,5-dimethyl-8-methoxy-5H-pyrido[4,3-b]indole dihydrochloride obtained in example 19 is added to 30 ml of a 48% aqueous solution of hydrobromic acid, and the medium is taken to reflux for 3 hours. The solution is then concentrated under reduced pressure. The crude product obtained is washed with acetone and then purified by chromatography on a column of silica (eluent: methanol/triethylamine; 9/1). The pure base is then converted into hydrochloride according to the operating method of example 12. Thus 2.1 g of expected hydrochloride is isolated.

Yield: 75%; m.p.=260° C.

Calculated for $C_{19}H_{28}N_4OCl_2$; 1$H_2O$: C, 54.67; H, 7.19; N, 13.42; Cl, 17.00. Found: C, 54.40; H, 7.29; N, 13.15; Cl, 16.71.

NMR H1 ($D_2O$); δ: 1.47 (t, 2×3H,$CH_2$—$CH_3$), 2.40 (d, 3H,$CH_3$-4,J 3.34–3.62 (m, 3×2H,$CH_2$—$CH_3$ and $CH_2$-β), 3.47 (s, 3H,$CH_3$-5), 3.84–4.03 (m, 2H,$CH_2$-α), 6.86 (q, 1H,H-7,$J_{7-6}$=8.9 Hz, $J_{7-9}$=2.2 Hz), 7.02 (d, 1H,H-6), 7.19 (d, 1H,H-9), 7.33 (d, 1H,H-3).

EXAMPLE 21

Preparation of 4,5-dimethyl-1-(3-dimethylamino-2-methyl-propylamino)-8-methoxy-5pyrido[4,3-b]i dihydrochloride, SR 26165 A (derivative no. 20) (I: $R_1=CH_3$, $R_2=OCH_3$, $R_3=R_4=CH_3$, $R_5=H$, $R_5R_5=H$, n=3)

This compound is prepared according to the operating method of example 19 in the presence of 3-dimethylamino-2-methylpropylamine.

Yield: 66%; m.p.=220° C.

Calculated for $C_{20}H_{30}N_4OCl_2$; 1.75$H_2O$: C, 53.99; H, 7.59; N, 12.60. Found: C, 53.86; H, 7.67; N, 12.34.

NMR H1 ($D_2O$); δ: 1.41 (d, 3H,CH—$CH_3$), 2.53 (s, 3H,$CH_3$-4), 2.61–2.93 (m, 1H,CH), 3.22 (s, 2×3H,N—$CH_3$), 3.37–3.81 (m, 2×2H,$CH_2$-γ and $CH_2$-α), 3.52 (s, 3H,$CH_3$-5), 4.09 (s, 3H,$OCH_3$), 7.16 (q, 1H,H-7,$J_{7-6}$=9 Hz, $J_{7-9}$=2 Hz), 7.34 (d, 1H,H-6), 7.53 (d, 1H,H-9), 7.58 (s, 1H,H-3).

EXAMPLE 22

Preparation of 4,5-dimethyl-1-(3-dimethylamino-2-methyl-propylamino)-8-hydroxy-5H-pyrido[4,3-b]dihydrochloride, SR 26166 A (derivative no. 21) (I: $R_1=CH_3$, $R_2=OH$, $R_3=R_4=CH_3$, $R_5-=H$, $R_5-=CH_3$, $R_5-=H$, n=3)

This compound is prepared according to the operating method of example 20 starting from 4,5-dimethyl-1-(3-dimethylamine-2-methylpropylamino)-8-methoxy-5H-pyrido[

Yield: 67%; m.p.=236° C.

Calculated for $C_{19}H_{28}N_4OCl_2$; 2.25$H_2O$: C, 51.87; H, 7.44; N, 12.73. Found: C, 52.07; H, 6.97; N, 12.71.

NMR H1 ($D_2O$); δ: 1.23 (d, 3H,CH—$H_3$), 2.38 (d, 3H,$CH_3$-4,$JH$3-$CH_3$- 2.53–2.71 (m, 1H,CH), 3.04 (s, 2×3H,N—$CH_3$), 3.23 (d, 2H,$CH_2$-γ), 3.49–3.60 (q, 2H,$CH_2$-α, 3.64 (s, 3H,$CH_3$-5), 7.05 (q, 1H,H-7,$J_{7-6}$=$J_{7-9}$=2 Hz), 7.21 (d, 1H,H-6), 7.25 (d, 1H,H-9), 7.34 (d, 1H,H-3).

EXAMPLE 23

Preparation of 1-(4-diethylaminobutylamino)-4,5-dimethyl-8-methoxy-5H-pyrido[4,3-b]indole dihydrochloride, SR 26180 A (derivative no. 22) (I: $R_1=CH_3$, $R_2=OCH_3$, $R_3=R_4=C_2H_5$, $R_5=H$, n=4

This compound is prepared according to the operating method of example 19 in the presence of 4-diethylaminobutylamine. The hydrochloride is obtained in an isopropanol medium.

Yield: 26%; m.p.=232° C.

Calculated for $C_{22}H_{34}N_4OCl_2$; 0.25$H_2O$: C, 59.25; H, 7.80; N, 12.56. Found: C, 59.08; H, 7.87; N, 12.45.

NMR H1 ($D_2O$); δ: 1.28 (t, 2×43H,$CH_2$—$CH_3$), 1.72–1.97 (m, 2×2H,CH2-βCH2-γ), 2.47 (s, 3H,$CH_3$-4), 3.09–3.36 (m, 3×2H, $CH_2$—$CH_3CH_2$-δ), (m, 2H,$CH_2$-α), 3.81 (s, 3H,$CH_3$-5), 3.97 (s, 3H,$OCH_3$), 7.20 (q, 1H,H-7, $J_7$=9 Hz,$J_{7-9}$=2 Hz), 7.34 (d, 1H,H-6), 7.37 (d, 1H,H-9), 7.47 (s, 1H,H-3).

EXAMPLE 24

Preparation of
1-(4-diethylaminobutylamino)-4,5-dimethyl-8-hydroxy-5H-pyrido[4,3-b]indole dihydrochloride, SR 26181 A (derivative no. 23) (I: $R_1=-CH_3$, $R_2=OH$, $R_3=R_4=C_2H_5$, $R_5=H$, $n=4$)

This compound is prepared according to the operating method of example 20 starting from 1-(4-diethylaminobutylamino) 4,5-dimethyl-8-methoxy-5H-pyrido[4,3-b]indo The hydrochloride is obtained in an isopropanol medium.

Yield: 44%; m.p.=180° C.

Calculated for $C_{21}H_{32}N_4OCl_2$; $2.75H_2O$: C, 52.90; H, 7.93; N, 11.75. Found: C, 53,12; H, 7.78; N, 11.59.

NMR H1 (D2O); δ: 1.28 (t, 2×3H,CH2—CH3), 1.69–1.91 (m, 2×2H,CH2-βCH2-γ), 2.28 (s, 3H,CH3-4), 3.08-3.41 (4×2H,CH2—CH3,CH2-δ and 3.47 (s, 3H,CH3-5), 6.86 (q, 1H,H-7,J7-6=9 Hz, J7-9R=2 Hz), 7.00 (d, 1H,H-6), 7.12 (d, 1H,H-9), 7.19 (s, 1H,H-3).

EXAMPLE 25

Preparation of
1-(3-diethylamino-2-hydroxypropylamino)-4,5-dimethyl-8-hydroxy-5H-pyrido[4,3-b]SR 95964 (derivative no. 24) and its dihydrochloride, SR 95964 A (derivative no. 25) (I: $R_1=CH_3$, $R_2=OH$, $R_3=R_4=C_2H_5$, $R_5$-α=H, $R_5$-β=OH, $R_5$-γ=H, n=3)

This compound is prepared according to the operating method of example 12 starting from 4,5-dimethyl-1-chloro-8-hydroxy-5H-pyrido[4,3-b]indole obtained according to example 5 in the presence of 3-diethylamino-2-hydroxypropylamine. The base is simply purified by recrys from toluene.

Yield: 59%; m.p.=180°–181° C.

Calculated for $C_2.H_{20}N_4O_2$; $0.2H_2O$: C, 66.74; H, 7.90; N, 15.57. Found: C, 66.74; H, 7.94; N, 15.40.

NMR H1 [(CD3)2SO]: δ: 1.00 (t, 2×3H,CH2—CH3), 2.53 (m, 2×2H,CH2.61 (d, 3H,CH3-4,JCH3-4-H3=0.4 Hz), 3.63 (m, 4H,2×2H,CH2-α,CH3.84 (m, 1H,CH—OH), 4.03 (s, 3H,CH3-5), 5.24 (s, 1H,-OH), 6.10 (t, 1H,NH), 6.97 (q, 1H,H-7,J7-6=8.4 Hz, J7-9=1.8 Hz), 7.38-7.50 (m, 2H,H-6+H-9), 7.64 (d, 1H,H-3), 9.02 (s, 1H,OH-8).

The hydrochloride is prepared according to the method described in example 12.

Yield: 92%; m.p.=250° C.

Calculated for $C_{20}H_{30}N_4O_2Cl_2$; $0.75H_2O$: C, 54.29; H, 7.17; N, 12.66. Found: C, 54.16; H, 7.06; N, 16.61.

The results of the pharmacological and toxicological studies mentioned hereafter, are evidence of the useful properties of the derivatives of the invention, both as regards toxicity and tolerance, and as regards their antitumour activity.

The subject of the invention is also a medicament showing, in particular, an antitumour activity, characterized in that it contains as active principle a derivative with the formula (I) and its tautomeric forms as well as the addition salts with pharmaceutically acceptable mineral or organic acids.

TOXICOLOGICAL STUDY

The compounds of the invention benefit from a good tolerance and a weak toxicity.

Thus the administration, to healthy CDF1 hybrid mice, in a single injection by intraperitoneal route, of the compounds under test, has enabled it to be established that the product is perfectly tolerated at a high dosage since the survival rate of the animals of the experiment was 100 out of 100 thirteen days after administration.

The results are summarized in the following table.

| Derivative | Dose mg/kg | Percentage of survivors thirteen days after administration |
|---|---|---|
| No. 1 | 100 | 100 |
| No. 4 | 50 | 100 |
| No. 7 | 50 | 100 |
| No. 10 | 100 | 100 |
| No. 11 | 50 | 100 |
| No. 14 | 25 | 100 |

In addition the administration, to healthy female CDF1 hybrid mice, in a single injection by intravenous route with a perfusor, lasting 4 minutes, of the compounds under test in solution in physiological serum at a rate of 0.1 ml of solution per 10 g weight of the animals has enabled it to be established that the compounds are also well tolerated at a high dosage in these conditions.

The results are summarized in the following table.

| Derivative | Dose mg/kg | Percentage of survivors eight days after administration |
|---|---|---|
| No. 7 | 25 | 100 |
|  | 30 | 100 |
| No. 10 | 25 | 100 |
|  | 40 | 40 |
| No. 11 | 40 | 100 |
|  | 50 | 100 |
| No. 14 | 50 | 100 |

The toxicity has also been evaluated by following, throughout the tests, the mortality and the weight development of the animals of the experiment. Is was noted, as is mentioned further on, that at the effective doses, the compounds of the invention were well tolerated and that the therapeutic indication was clearly favourable.

PHARMACOLOGICAL STUDY

This was carried out in vitro and in vivo.

(1) In vitro: (PAOLETTI et al., Chem. Biol. Interaction, 1979, 25, 45–58).

The cytotoxic activity of the compounds of the invention has been evaluated by in vitro tests. These tests consist of adding increasing concentrations of the compound under test to a cellular culture of the leukemia tumour line L 1210 in an exponential phase of growth. The cellules are incubated at 37° C. in a $CO_2$ incubator and counted every 24 hours. The calculation of the I D 50 (concentration of the product, expressed in $1^{-1}$ micromole, which inhibits the proliferation of the cells by 50%) is made after 48 hours contact.

Determined in this way, the I D 50 of the compounds of the invention are summarized in the following table:

| Derivative | I D 50 Micromole $1^{-1}$ |
|---|---|
| 1 | 0.20 |
| 2 | 0.16 |
| 3 | 1.14 |
| 4 | 0.30 |
| 5 | 1.20 |
| 6 | 0.10 |

-continued

| Derivative | I D 50 Micromole $l^{-1}$ |
|---|---|
| 7 | 0.06 |
| 8 | 0.08 |
| 9 | 0.09 |
| 11 | 0.03 |
| 12 | 0.035 |
| 13 | 0.13 |
| 14 | 0.014 |
| 15 | 0.01 |
| 16 | 0.72 |
| 17 | 0.35 |
| 18 | 1.20 |
| 19 | 0.15 |
| 20 | 1.00 |
| 21 | 0.01 |
| 22 | 1.30 |
| 23 | 0.31 |
| 25 | 0.063 |

(2) In vivo: (GERAN et al., Cancer Chemother., 1972, 2, 07-57):

The antitumour activity was tested in vivo on various tumours inoculated in various ways according to the following general protocol:

All the male or female mice are inoculated on day D0 with a known quantity of viable tumour cells for ascitic tumours or with a known tumour fragment for solid tumours.

They are then distributed into various groups. Each group, corresponding to the animals treated by the product under test, is made up of 10 mice. The product under test is dissolved in distilled water and it is administered n times (Dx-Dy), n, y, and x varying according to the protocol chosen, at the rate of 0.1 ml of solution per 10 g by weight of mice treated and at specific doses for each protocol.

The "negative control" group, corresponding to the animals which are not treated by the product, contains $2\sqrt{N}$ animals, N being equal to or greater than the total number of mice treated by the product in the same experiment.

Finally, the tests can also be carried out at the same time as the study of a group called "positive control", of ten animals, which is treated by a molecule, known for its antitumour activity and which can vary according to the protocol chosen, in the same conditions as the groups treated by the product under test.

The antitumour activity is evaluated, in the case of ascitic tumours, by considering the increase in the survival time of the animals treated in comparison to that of the animals in the "negative control" group, according to the formula:

$$T/C = \frac{\text{Median day of survival for animals in the group treated with a given dose of product}}{\text{Median day of survival for animals in the "negative control" group}} \times 100$$

The criterion for activity varies according to the protocol.

Also, a product is considered as toxic at the dose studied when this T/C value is equal to or less than 85%. In addition, a product is also considered as toxic at the dose studied when the weight variation, expressed in grams and calculated by the formula:

"Average weight of the group measured on day 5—Average weight of the same group measured on day 1"

is equal to or less than 4 g.

the antitumour activity is evaluated, in the case of solid tumours, by considering the reduction in the average tumour volume of the treated animals in comparison with the animals of the "negative control" group, according to the formula:

$$T/C = \frac{\text{Average tumour volume of animals in the group treated with a given dose of product and on day } D}{\text{Average tumour volume of the "negative control" group measured on the same day}} \times 100$$

A value for T/C of less than 42% indicates an activity for the product at the studied dose.

(a) Test of lelukemia P 388; IP/IP, D1-5 (GERAN et al., Cancer Chemother., 1972, 2, 07-57).

The tests are carried out with $CDF_1$ hybrid mice inoculated by intraperitoneal route with $10^6$ leukemia cells from the P 388 line. The compound under test is administered for 5 successive days (D1-D5) by intraperitoneal route. The positive control for the test is 5-fluorouracile which is administered in the same conditions. The number of surviving animals is evaluated on day D30. A compound is considered as active when the T/C ratio is greater than 127%.

The results obtained are recorded in the following table no. 1.

TABLE NO. 1

| Product tested | Dose (mg/kg) | Variation by weight (g) | Median day of survival | T/C % | Number of survivors |
|---|---|---|---|---|---|
| Derivative No. 1 | 10 | −0.9 | 15.7 | 130 | 0/10 |
|  | 50 | −2.6 | 21.0 | 174 | 0/10 |
| Positive control: 5-Fluorouracile | 20 | +1.3 | 20.1 | 166 | 0/10 |
| Negative control | — | −0.8 | 12.1 | — | 0/36 |
| Derivative No. 4 | 5 | +1.1 | 14.0 | 121 | 0/10 |
|  | 10 | +0.7 | 17.0 | 147 | 0/10 |
|  | 20 | −0.9 | 17.25 | 149 | 0/10 |
|  | 40 | −3.4 | 20.3 | 176 | 0/10 |
|  | 80 | −4.8 | 6.6 | 57 | 0/10 |
| Positive control: 5-Fluorouracile | 20 | +0.3 | 18.9 | 164 | 0/10 |
| Negative control | — | +1.0 | 11.55 | — | 0/30 |
| Derivative No. 7 | 0.625 | +0.3 | 14.3 | 127 | 0/10 |
|  | 1.25 | +0.3 | 17.25 | 153 | 0/10 |
|  | 2.5 | +0.1 | 18.25 | 162 | 0/10 |
|  | 5 | +0.3 | 19.25 | 170 | 0/10 |
|  | 10 | −0.2 | 20.9 | 185 | 0/10 |
|  | 15 | +1.6 | 23.55 | 208 | 3/10 |

TABLE NO. 1-continued

| Product tested | Dose (mg/kg) | Variation by weight (g) | Median day of survival | T/C % | Number of survivors |
|---|---|---|---|---|---|
| | 20 | −1.1 | 27.0 | 238 | 1/10 |
| | 30 | 0.0 | 9.25 | 81 | 0/10 |
| Positive control: 5-Fluorouracile | 20 | +0.6 | 19 | 168 | 0/10 |
| Negative control | — | +4.0 | 11.3 | — | 0/10 |
| Derivative No. 8 | 0.625 | −0.5 | 15.1 | 136 | 0/10 |
| | 1.25 | +0.6 | 15.7 | 141 | 0/10 |
| | 2.5 | −1.2 | 16.1 | 147 | 0/10 |
| | 5 | −0.8 | 19.4 | 175 | 0/10 |
| | 10 | −1.1 | 12.0 | 108 | 0/10 |
| Positive control: 5-Fluorouracile | 20 | −0.8 | 17.75 | 160 | 0/10 |
| Negative control | — | +0.2 | 11.1 | — | 0/20 |
| Derivative No. 10 | 0.625 | +4.1 | 15.75 | 139 | 0/10 |
| | 1.25 | +3.3 | 17.0 | 150 | 0/10 |
| | 2.5 | +3.2 | 16.4 | 145 | 0/10 |
| | 5 | +2.0 | 21.0 | 186 | 1/10 |
| | 10 | +1.8 | 16.75 | 148 | 0/10 |
| | 20 | −0.4 | 7.8 | 69 | 0/10 |
| Positive control: 5-Fluorouracile | 20 | +3.7 | 16.7 | 147 | 0/10 |
| Negative control | — | +4.0 | 11.3 | — | 0/25 |
| Derivative No. 11 | 2.5 | +1.2 | 17.25 | 149 | 0/10 |
| | 5 | +0.7 | 19.25 | 166 | 0/10 |
| | 10 | +0.2 | 23.75 | 205 | 2/10 |
| | 20 | −2.8 | 7.4 | 64 | 0/10 |
| Positive control: 5-Fluorouracile | 20 | +1.3 | 20.1 | 173 | 0/10 |
| Negative control | — | +1.0 | 11.56 | — | 0/20 |
| Derivative No. 12 | 1.25 | −0.5 | 16.7 | 152 | 1/10 |
| | 2.5 | −1.2 | 18.0 | 164 | 0/10 |
| | 5 | −1.9 | 19.00 | 173 | 2/10 |
| | 10 | −3.5 | 19.3 | 176 | 0/10 |
| | 20 | −5.9 | 9.7 | 88 | 0/10 |
| Positive control: 5-Fluorouracile | 20 | −0.1 | 18.8 | 171 | 0/10 |
| Negative control: | — | −0.95 | 11.0 | — | 0/20 |
| Derivative No. 13 | 5 | +1.0 | 14.1 | 134 | 0/10 |
| | 10 | +1.2 | 16.8 | 160 | 0/10 |
| | 20 | +0.4 | 15.8 | 150 | 0/10 |
| | 40 | −2.5 | 8.4 | 80 | 0/10 |
| Negative control | — | +2.1 | 10.5 | — | 0/25 |
| Derivative No. 14 | 2.5 | +0.9 | 19.25 | 166 | 1/10 |
| | 5 | −1.0 | 22 | 190 | 3/10 |
| | 10 | −1.7 | 11.75 | 102 | 0/10 |
| | 20 | −4.4 | 7.4 | 64 | 0/10 |
| Positive control: 5-Fluorouracile | 20 | +1.2 | 20 | 173 | 0/10 |
| Negative control | — | +1.0 | 11.56 | — | 0/20 |
| Derivative No. 15 | 1.25 | −1.9 | 18.0 | 164 | 0/10 |
| | 2.5 | −1.9 | 20.25 | 184 | 0/10 |
| | 5 | −2.5 | 26 | 236 | 1/10 |
| | 10 | −4.1 | 9.3 | 85 | 0/10 |
| Positive control: 5-Fluorouracile | 20 | −0.2 | 17 | 154 | 0/10 |
| Negative control | — | −0.95 | 11.0 | | 0/20 |
| Derivative No. 17 | 24 | 0.0 | 15.4 | 131 | 0/10 |
| Negative control | — | −0.1 | 11.8 | — | 0/25 |
| Derivative No. 19 | 5 | +0.5 | 15.3 | 142 | 0/6* |
| | 10 | −0.2 | 17.0 | 153 | 0/6* |
| | 20 | +0.3 | 20.3 | 182 | 0/6* |
| | 40 | −2.1 | 15.3 | 137 | 0/6* |
| Positive control: 5-Fluorouracile | | | | | |
| Negative control | — | +0.1 | 11.1 | — | 0/23 |

*As an exception this experiment was carried out on groups of 6 treated animals.

(b) Test for Leukemia P388, IP/IP, D1 (GERAN et al. Cancer chemother., 1972, 2, 07-57).

The test is carried out according to the preceding protocol, the compound under test being administered only on day D1.

The results obtained are recorded in the following table no. 2.

TABLE NO. 2

| Product tested | Dose (mg/kg) | Variation by weight (g) | Median day of survival | T/C % | Number of survivors |
|---|---|---|---|---|---|
| Derivative No. 7 | 10 | +1.2 | 15.1 | 129 | 0/10 |

TABLE NO. 2-continued

| Product tested | Dose (mg/kg) | Variation by weight (g) | Median day of survival | T/C % | Number of survivors |
|---|---|---|---|---|---|
| | 20 | +0.2 | 16.25 | 139 | 0/10 |
| | 40 | −0.2 | 15.9 | 136 | 0/10 |
| | 80 | −1.7 | 2.3 | 20 | 0/10 |
| Negative control | — | +1.1 | 11.7 | — | 0/20 |
| Derivative No. 10 | 5 | −0.1 | 15.3 | 139 | 0/10 |
| | 10 | +0.3 | 15.25 | 139 | 0/10 |
| | 20 | −0.8 | 15.6 | 142 | 0/10 |
| | 40 | −1.4 | 15.3 | 139 | 0/10 |
| Positive control: 5-Fluorouracile | 200 | −3.2 | 19.0 | 173 | 0/10 |
| Negative control | — | +0.8 | 11.0 | — | 0/20 |
| Derivative No. 12 | 5 | +0.1 | 15.87 | 139 | 0/10 |
| | 10 | −0.6 | 17.75 | 156 | 0/10 |
| | 20 | −1.2 | 20.75 | 182 | 0/10 |
| | 40 | −6.2 | 23.0 | 202 | 1/10 |
| Derivative No. 14 | 5 | −1.2 | 19.75 | 173 | 0/10 |
| | 10 | −1.4 | 19.0 | 167 | 1/10 |
| | 20 | −2.5 | 18.75 | 164 | 1/10 |
| Negative control | — | −0.05 | 11.4 | — | 0/20 |

(c) Test for leukemia L 1210, IP/IP, D-5 (GERAN et al., Cancer cheomother., 1972, 2, 07-57).

The tests are carried out with CDF$_1$ hybrid mice inoculated by intraperitoneal route with $10^5$ leukemia cells from the L 1210 line. The compound under test is administered for 5 days (D1-D5) by intraperitoneal route. The positive control for the test is 5-fluorouracile administered in the same conditions. The number of surviving animals is evaluated on day D60. A compound is considered as being active when the T/C ratio is greater than or equal to 125%.

The results obtained are shown in the following table no. 3:

(d) Test for melanoma B 16 (GERAN et al., Cancer Chemother., 1972, 2, 07-75).

The tests are carried out with BDF$_1$ hybrid mice inoculated by intraperitoneal route with 0.5 ml of a homogenate of melanoma B 16 made up from 1 g of tumour in 10 ml of physiological serum. The compound under test is administered for 9 days (D1-D9) by intraperitoneal route. The positive control for the test is Cis-Platine administered in the same conditions. The number of surviving animals is evaluated on day D60. A compound is considered as being effective when the T/C ratio is greater than or equal to 125%.

The results obtained are summarized in the following table no. 4:

TABLE NO. 3

| Product tested | Dose (mg/kg) | Variation by weight (g) | Median day of survival | T/C % | Number of survivors |
|---|---|---|---|---|---|
| Derivative No. 7 | 0.625 | −0.9 | 11.75 | 133 | 0/10 |
| | 1.25 | −1.2 | 14.25 | 162 | 0/10 |
| | 2.5 | −1.1 | 20.75 | 236 | 4/10 |
| | 5.0 | −0.8 | 14.0 | 159 | 2/10 |
| | 10 | −2.2 | 37.0 | 420 | 5/10 |
| | 20 | −4.2 | 35.0 | 398 | 5/10 |
| | 30 | −5.6 | 8.25 | 94 | 0/10 |
| Positive control: 5-Fluorouracile | 20 | −0.5 | 16.0 | 182 | 0/10 |
| Negative control: | — | −0.8 | 8.8 | — | 0/25 |
| Derivative No. 10 | 1.25 | −1.7 | 12.75 | 145 | 1/10 |
| | 2.5 | −2.1 | 20.0 | 227 | 4/10 |
| | 5 | −2.7 | >60 | >682 | 6/10 |
| | 10 | −3.1 | 15.25 | 173 | 4/10 |
| | 20 | −5.6 | 8.4 | 95 | 0/10 |
| Positive control: 5-Fluorouracile | 20 | −0.5 | 16.0 | 182 | 0/10 |
| Negative control | — | −0.8 | 8.8 | — | 0/25 |

TABLE NO. 4

| Product tested | Dose (mg/kg) | Variation by weight (g) | Median day of survival | T/C % | Number of survivors |
|---|---|---|---|---|---|
| Derivative No. 4 | 5 | −1.9 | 29.0 | 135 | 0/10 |
| Negative control | — | −1.0 | 21.5 | — | 0/20 |
| Derivative No. 7 | 2.5 | +3.6 | 34 | 124 | 0/10 |
| | 5 | −0.1 | 48 | 174 | 0/10 |
| | 10 | +1.6 | 56.25 | 205 | 4/10 |
| | 20 | −0.8 | 58 | 211 | 5/10 |
| | 30 | −1.0 | 9.0 | 33 | 0/10 |
| Positive control: Cis-Platine | 0.5 | −0.6 | 36 | 131 | 0/10 |
| Negative control | — | +2.1 | 27.5 | — | 0/25 |
| Derivative No. 9 | 0.625 | +1.3 | 28 | 118 | 0/10 |
| | 1.25 | +0.1 | 33.0 | 139 | 1/10 |

TABLE NO. 4-continued

| Product tested | Dose (mg/kg) | Variation by weight (g) | Median day of survival | T/C % | Number of survivors |
|---|---|---|---|---|---|
| | 2.5 | +0.8 | 31.25 | 131 | 1/10 |
| Positive control Cis-Platine | 0.5 | −0.6 | 30.0 | 126 | 0/10 |
| Negative control | — | +0.8 | 23.8 | — | 0/30 |
| Derivative No. 10 | 1.25 | +2.8 | 32.0 | 116 | 0/10 |
| | 2.5 | +1.8 | 38.75 | 141 | 0/10 |
| | 5 | +2.4 | 44.0 | 160 | 0/10 |
| | 10 | +0.5 | 11.7 | 42 | 0/10 |
| Positive control Cis-Platine | 0.5 | −0.6 | 38.75 | 141 | 0/10 |
| Negative control | — | +2.1 | 27.5 | — | 0 |
| Derivative No. 11 | 1.25 | −2.5 | 32.25 | 133 | 0/10 |
| | 2.5 | +0.6 | 35.25 | 145 | 0/10 |
| | 5 | +0.2 | 41.25 | 170 | 3/10 |
| | 10 | −1.0 | 19.3 | 79 | 0/10 |
| Derivative No. 14 | 1.25 | +1.0 | 29.75 | 123 | 0/10 |
| | 2.5 | +0.1 | 32.6 | 134 | 0/10 |
| | 5 | −0.2 | 50.0 | 206 | 1/10 |
| | 10 | −1.9 | 11.75 | 48 | 0/10 |
| Negative control | — | −2.0 | 24.75 | — | 0/25 |

(e) Test for reticulosarcoma M5-M5076 (N.C.I. Protocol 3 M., 531, p 1–7, 23.5.1983).

The tests are carried out with $BDF_1$ hybrid mice inoculated by intraperitoneal route with $10^6$ cells of the M5-M5076 line. The compound under test is administered 5 times successively in sequence (D1,5,9,13,17) by intraperitoneal route. The positive control for the test is cyclophosphamide administered in the same conditions. The number of surviving animals is evaluated on day D75. A compound is considered as active when the T/C ratio is greater than or equal to 125%.

The results obtained are recorded in the following table no. 5:

TABLE NO. 5

| Product tested | Dose (mg/kg) | Variation by weight (g) | Median day of survival | T/C % | Number of survivors |
|---|---|---|---|---|---|
| Derivative No. 1 | 50 | −0.6 | 32.7 | 130 | 0/10 |
| Positive control: Cyclopnospnamide | 160 | −1.9 | >60 | >239 | 9/10 |
| Negative control | — | +1.8 | 25.1 | — | 0/40 |
| Derivative No. 7 | 2.5 | −1.0 | 31.25 | 120 | 0/10 |
| | 5 | −1.4 | 33.0 | 127 | 1/10 |
| | 10 | −1.8 | 37.25 | 143 | 0/10 |
| | 20 | −1.9 | 41.0 | 158 | 0/10 |
| | 40 | −1.8 | 42.0 | 161 | 1/10 |
| Positive control: Cyclopnospnamide | 160 | −4.9 | 57.0 | 219 | 0/10 |
| Negative control | — | −0.8 | 26.0 | — | 0/30 |
| Derivative No. 10 | 1.25 | +2.7 | 34.0 | 133 | 1/10 |
| | 2.5 | +0.4 | 33.0 | 129 | 1/10 |
| | 5 | +2.1 | 40.0 | 156 | 1/10 |
| | 10 | +1.2 | 42.0 | 164 | 1/10 |
| | 20 | 0.0 | 44.75 | 175 | 1/10 |
| | 40 | −2.8 | 46.0 | 180 | 2/10 |
| Positive control: Cyclopnospnamide | 160 | −1.9 | >60 | >234 | 9/10 |
| Negative control | — | +1.0 | 25.6 | — | 0/20 |

(f) Test for leukemia P 388 IP/D1 IV (GERAN et al., Cancer Chemother., 1972, 2, 07-57).

The test is carried out according to the same protocol as that described for test (a), the compound under test being administered by intravenous route only on day D1.

The results obtained are recorded in the following table no. 6:

TABLE NO. 6

| Product tested | Dose mg/kg | Variation by weight (g) | Median day of survival | T/C % | Number of survivors |
|---|---|---|---|---|---|
| Deriv. no. 12 | 50 | −0.7 | 19.0 | 174 | 0/10 |
| | 100 | −1.6 | 24.3 | 223 | 1/10 |
| Deriv. no. 15 | 50 | +0.5 | 17.75 | 163 | 1/10 |
| | 100 | −0.25 | 25.75 | 236 | 4/10 |
| Negative Control | — | +3.5 | 10.90 | — | — |

(g) Test for leukemia L 1210 IP/D1 IV. (GERAN et al., Cancer Chemother., 1972, 2, 07-57).

The test is carried out according to the same protocol as that described for test (c), the compound under test being administered by intravenous route only on day D1.

The results obtained are recorded in the following table no. 7:

TABLE NO. 7

| Product tested | Dose mg/kg | Variation by weight (g) | Median day of survival | T/C % | Number of survivors |
|---|---|---|---|---|---|
| Deriv. no. 11 | 20 | −0.4 | 11.8 | 132 | 0/10 |

TABLE NO. 7-continued

| Product tested | Dose mg/kg | Variation by weight (g) | Median day of survival | T/C % | Number of survivors |
|---|---|---|---|---|---|
|  | 40 | −0.2 | 13.3 | 149 | 0/10 |
| Deriv. no. 14 | 20 | −1.1 | 14.0 | 157 | 0/10 |
| Negative Control | — | +0.8 | 8.9 | — | 0/15 |

(h) Test for colic adenocarcinoma 38, SC/D1 IV. (GERAN et al., Cancer Chemother., 1972, 2, 07-57).

The tests are carried out with $BDF_1$ hybrid mice inoculated by subcutaneous route with a standardized tumour fragment of 3 $mm^3$. The compound under test is administered by intravenous route only on day D1.

The number of surviving animals is evaluated on day D38.

The results obtained are assembled in table no. 8.

TABLE NO. 8

| Product tested | Dose mg/kg | Average tumour volume at D38 | T/C % at D38 | Number of survivors |
|---|---|---|---|---|
| Deriv. no. 12 | 100 | 3.24 | 36 | 10/10 |
| Deriv. no. 15 | 50 | 2.73 | 30 | 10/10 |
| Negative Control | — | 8.94 | — | 5/10 |

(i) Test for colic adenocarcinoma 38, SC/D2,9 IV (GERAN et al., Cancer Chemother., 1972, 2, 07-57).

This test is carried out according to the protocol described for test (h), the compound under test being administered by intravenous route on day D2 then on day D9.

The number of surviving animals is evaluated on day D32.

The results obtained are recorded in the following table no. 9:

TABLE NO. 9

| Product tested | Dose mg/kg | Average tumour volume at D32 | T/C % at D32 | Number of survivors |
|---|---|---|---|---|
| Deriv. no. 12 | 50 | 1.38 | 18 | 10/10 |
|  | 75 | 0.97 | 13 | 10/10 |
| Deriv. no. 15 | 25 | 0.0 | 0 | 10/10 |
|  | 50 | 0.0 | 0 | 10/10 |
| Negative Control | — | 7.51 | — | 5/10 |

The toxicological and pharmacological studies which have just been mentioned are evidence of the useful antitumour properties of the compounds of the invention, which make them very useful in therapeutics.

The medicament of the invention can be presented for oral administration in the form of tablets, sugar-coated tablets, capsules, drops or syrup. They can also be presented for rectal administration in the form of suppositories and for parenteral administration in the form of an injectable solution by intramuscular or intravenous route.

Each unitary dose advantageously contains from 0.005 g to 0.400 g combined with suitable excipients and vehicles, the doses which can be administered daily can vary from 0.005 g to 3.00 g of active principle, as a function of the weight of the invalid, of his age and of the seriousness of his condition.

As non-limiting examples, there are given below a few pharmaceutical formulations of the medicament of the invention.

| (1) Sugar-coated tablets | |
|---|---|
| Derivative no. 4 | 0.250 g |

Excipient: kaolin, lactose, magnesium carbonate, gum arabic, corn starch, saccharose, gelatin, white wax.

| (2) Tablets | |
|---|---|
| Derivative no. 9 | 0.300 g |

Excipient: corn starch, lactose, magnesium stearate, talc.

| (3) Capsules | |
|---|---|
| Derivative no. 1 | 0.150 g |

Excipient: magnesium stearate, talc, aerosil.

| (4) Suppositories | |
|---|---|
| Derivative no. 7 | 0.250 g |

Excipient: semi-synthetic triglycerides q.s. for 1 suppository.

| (5) Injectable solution | |
|---|---|
| Derivative no. 11 (dimaleate) | 0.400 g |
| Derivative no. 15 (dihydrochloride) | 0.100 g |

Excipient: isotonic solvent q.s. for 10 ml.

For its antitumour properties, the medicament of the invention is indicated in the treatment of solid tumours and of their metastases as well as in the treatment of leukemias.

We claim:

1. A compound selected from the compounds having the formula

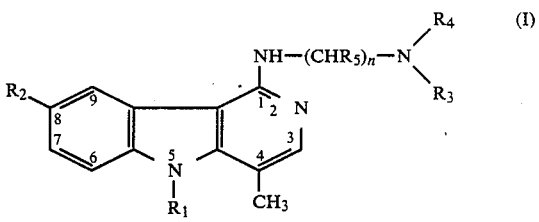

in which n represents a whole number from 2 to 4, $R_1$ is selected from hydrogen and $C_1-C_4$ alkyl, $R_2$ is selected from hydrogen, hydroxy and $C_1-C_4$ alkoxy, $R_3$ and $R_4$, independently from each other, are selected from hydrogen, $C_1-C_4$ alkyl and hydroxyalkyl, $R_5$ can be identical or different and is selected from hydrogen, hydroxy and $C_1-C_4$ alkyl, as well as the tautomeric forms when they exist, and the addition salts with pharmaceutically acceptable mineral or organic acids.

2. 1-(3-Diethylamino propylamino)-4-methyl-5H-pyrido[4,3-b]indole and its pharmaceutically acceptable salts.

3. 1-(3-Diethylamino propylamino)-8-methoxy-4-methyl-5H-pyrido[4,3-b]indole and its pharmaceutically acceptable salts.

4. 1-(3-Diethylamino propylamino)-8-hydroxy-4-methyl-5H-pyrido[4,3-b]indole and its pharmaceutically acceptable salts.

5. 1-(3-Diethylamino propylamino)-8-hydroxy-4-methyl-5H-pyridol[4,3-b]indole and its pharmaceutically acceptable salts.

6. 1-(3-Diethylamino propylamino)-4,5-dimethyl-8-hydroxy-5H-pyrido-[4,3-b]indole and its pharmaceutically acceptable salts.

7. 4,5-Dimethyl-1-(3-dimethylamino propylamino)-8-hydroxy-5H-pyrido-[4,3-b]indole and its pharmaceutically acceptable salts.

8. 4,5-Dimethyl-1-(3-dimethylamino-2-methyl propylamino)-8-hydroxy-5H-pyrido[4,3-b]indole and its pharmaceutically acceptable salts.

9. 1-(2-Diethylamino ethylamino)-4,5-dimethyl-8-hydroxy-5H-pyrido-[4,3-b]indole and its pharmaceutically acceptable salts.

10. A therapeutic composition having an antitumoral activity comprising an effective amount of a compound as claimed in claim 1 in a mixture with a pharmaceutically acceptable excipient.

11. A therapeutic composition according to claim 10, wherein each unitary dose contains 0.005 g to 0.400 g of said compound.

12. A method for the treatment of melanoma, reticulosarcoma, and adenocarcinoma and their metastases which comprises administering to a human in need thereof an effective amount of a compound as claimed in claim 1.

13. A method for the treatment of leukemia which comprises administering to a human in need thereof an effective amount of a compound as claimed in claim 1.

* * * * *